United States Patent
Affeld

(10) Patent No.: US 6,432,100 B1
(45) Date of Patent: Aug. 13, 2002

(54) APPARATUS AND METHOD FOR GENERATION OF A PROTECTIVE SLEEVE AGAINST INFECTIONS FOR AN ARTIFICIAL LEAD

(76) Inventor: Ing Klaus Affeld, Niebuhrstr 11a, 10629 Berlin (DE)

( * ) Notice: Subject to any disclaimer, the term of this patent is extended or adjusted under 35 U.S.C. 154(b) by 0 days.

(21) Appl. No.: 09/437,861

(22) Filed: Nov. 10, 1999

(30) Foreign Application Priority Data

Nov. 11, 1998 (DE) ......................................... 198 52 848

(51) Int. Cl.⁷ ............................................. A61M 31/00
(52) U.S. Cl. .................. 604/500; 604/47; 604/174; 604/175; 604/104; 604/171; 604/265; 128/DIG. 26
(58) Field of Search ................................. 604/174, 175, 604/264, 523, 29, 28, 36, 43, 47, 500, 539, 502, 506, 513, 93.01, 104, 124, 171, 265, 540, 541, 543, 164.01, 164.09, 164.1, 164.11, 164.12; 606/214–215; 623/11; 128/DIG. 26

(56) References Cited

U.S. PATENT DOCUMENTS

| | | | |
|---|---|---|---|
| 4,479,795 A | * | 10/1984 | Mustacich et al. ............. 604/53 |
| 4,959,054 A | * | 9/1990 | Heimke et al. .............. 604/175 |
| 5,156,597 A | | 10/1992 | Verreet et al. |
| 5,308,338 A | * | 5/1994 | Helfrich ...................... 604/175 |
| 5,911,757 A | * | 6/1999 | Seare, Jr. ...................... 623/11 |

FOREIGN PATENT DOCUMENTS

| | | |
|---|---|---|
| CA | 2242033 | 1/1999 |
| DE | 39 43 412 A1 | 7/1991 |
| DE | 197 28 489 A1 | 1/1999 |

OTHER PUBLICATIONS

Christian Grosse–Siestrup and Klaus Affeld, "Design Criteria for Artificial Percutaneous Devices," Journal of Biomedical Materials Research, 1984, p. 357–382, vol. 18, John Wiley & Sons, Inc., USA.

* cited by examiner

Primary Examiner—Brian L. Casler
Assistant Examiner—Cris Rodriguez
(74) Attorney, Agent, or Firm—Christopher L. Parmelee; Walker & Jocke LPA

(57) ABSTRACT

An apparatus and method for generation of a protective sleeve against infections for a percutaneous lead through human or animal skin. The percutaneous lead (1) includes an extrusion port (7). When the lead extends through a body (3) of a patient, a pump (9) in operative connection with the lead is operative to move biocompatible liquid polymer material from a reservoir (10) through the extrusion port. As the polymer material comes in contact with body tissues of the patient it forms a protective sleeve against infections (5). The protective sleeve must be periodically clipped as it continuously or intermittently grows in an upward direction (6) outside of the body. The continual formation of the protective sleeve prevents the formation of a biofilm on the percutaneous lead that can cause the body tissue to separate from the percutaneous lead.

13 Claims, 3 Drawing Sheets

APPARATUS AND METHOD FOR GENERATION OF A PROTECTIVE SLEEVE AGAINST INFECTIONS FOR AN ARTIFICIAL LEAD

TECHNICAL FIELD

This invention relates to the generation of a protective sleeve against infections of a artificial lead that extends in the body of a patient. Specifically this invention relates to a new apparatus and method for the generation of a sterile protective sleeve for an percutaneous lead that extends through the skin of a human or animal patient.

BACKGROUND ART

A percutaneous lead is designed for an enduring connection between the external world and the inner space of the body. This is of importance for patients, who rely on such a connection for a diagnosis or a therapy. Such an application is, for example, the ambulant peritoneal dialysis. This treatment requires a permanent lead to the peritoneal cavity for the repeated exchange of dialysis fluid. This lead is sometimes called artificial lead through the skin or percutaneous lead.

Other applications are the artificial heart or an artificial cardiac assist system. These devices mostly require a tube penetrating the skin for the transport of air or electricity to energize the blood pump. A further application is the usage of the lead for the transport of biosignals, which are used for the stimulation of muscles or for sensory purposes.

All these long-term applications of an artificial lead through the skin are endangered by infection. Intense care of the percutaneous lead can alleviate these complication, but cannot completely eradicate the above mentioned dangers. Often percutaneous leads become so severely infected, that they have to be explanted. This operation endangers the life of the patient, if the infection invades deeply into the body.

The infections starts at the region, where the three phases—implant, body tissue and the microbe containing air—meet. That is the region, where the lead exits the body. At this three-phase line the microbes can be controlled initially by frequent cleansing and with bacteriostatica. But in the long-term, the microbes tend to form a biofilm at the surface of the artificial lead through the skin. This biofilm is a layer of microbes attached to the lead material. This layer protects itself by a mucus layer against the immune system. The body cannot fight against the infection because the biofilm is impenetrable for its defenses. The biofilm tends to expand. It grows in direction of the nutrition source. In this case, it is towards the inside of the body. As a result a pouch forms, which resists cleansing and which can result in a dangerous infection.

There are various artificial leads through the skin, which attempt to avoid this danger by a collar at the region where the lead exits the body. These collars are implanted just under the skin and should prevent the biofilm from invading. However, experience shows that the skin, nonetheless, retracts, exposing the collar and finally an infection can develop.

Further attempts have been made to avoid infections by covering the skin penetrating surface with porous surfaces, such as synthetic grafts, to encourage the ingrowth of cells. Clinical experience shows that these devices as well finally become infected.

In the patent DE 39 43 412 A1 the surface of the lead is covered by a porous textile, which is intended for an easy and sure ingrowth of cells by a decreasing porosity from the artificial surface to the tissue. Clinical experience shows, that this device as well finally becomes infected, because the tissue detaches from the artificial lead through the skin.

In the patent DE 197 28 489 A1 the surface of the lead is covered by an organic tissue made from collagen fibers or collagen polymer fibers. The basic idea is that the natural collagen encourages the ingrowth of tissue. Clinical experience shows that these devices as well finally become infected.

There are artificial leads through the skin with an easily movable three-phase line, which is made to reduce the mechanical force at the ingrowth cells. This is described in a publication of the inventor (Grosse-Siestrup, Ch., Affeld, K.: Design criteria for artificial percutaneous devices, Journal of Biomedical Materials Research, Vol 18, 357–382 (1984)). Clinical experience shows that these devices as well finally become infected in the long-term.

Hitherto all artificial leads through the skin can not prevent infections and the invading of microbes in the body in the long-term. They are accompanied with complications and endanger the patient.

DISCLOSURE OF INVENTION

It is an object of the present invention to provide a new percutaneous lead.

It is a further object of the present invention to provide a percutaneous lead that is operative to prevent infections.

It is a further object of the present invention to provide a percutaneous lead that is operative to prevent infections and microbes from invading the body It is a further object of the present invention to provide a percutaneous lead that is operative to prevent the formation of a biofilm at the surface of the artificial lead through the skin.

It is a further object of the present invention to provide a percutaneous lead that is operative to prevent body tissues from separating from the percutaneous lead.

Further objects of the present invention will be made apparent in the following Best Modes for Carrying Out Invention and the appended claims.

The foregoing objects are accomplished in one exemplary embodiment of the invention by a device that comprises a protective sleeve against infections at the three phase line, which is formed continuously or in intervals and which is moving out of the body. The sleeve imitates one prominent feature of natural percutaneous structures such as fingernails: Growth from the inside of the body to the outside.

The bacterial biofilm, which tends to form at the three-phase line, where the sleeve exits the skin, is pushed outwards into an area of lower humidity and lower nutrition. There the biofilm is perishing. The regeneration of the three-phase line is achieved by a protective sleeve against infections, which is created inside the microbe free body. This protective sleeve against infections surrounds the lead where it penetrates the skin and separates the lead from the surrounding tissue.

The protective sleeve against infections is formed by a liquid or plastic material, which hardens upon contact with water vapor or other substances from the body. This material is preferably injected from outside of the body to the inside by a tube. Such a material is for example the silicon rubber RTV 3140 of DOW Corning, which cures at room temperature under the influence of water vapor. In this invention, the vapor of the surrounding tissue is used.

There exist different materials, which are transformed to elastomeric polyurethane by this process. These materials can be mixed with biologically active substances, which are diffused inside the body. For example, it is possible to add antibiotics, to achieve a microbe free tissue. Other substances can promote the adhesion of cells at the protective sleeve against infections.

The protective sleeve against infections, which is formed continuously or in intervals as described above, requires cutting of unwanted extensions very much like hair and fingernails. The advantage of the invention is the complete prevention of infections in the region of the lead through the skin.

BEST MODES FOR CARRYING OUT INVENTION

Figure 1:
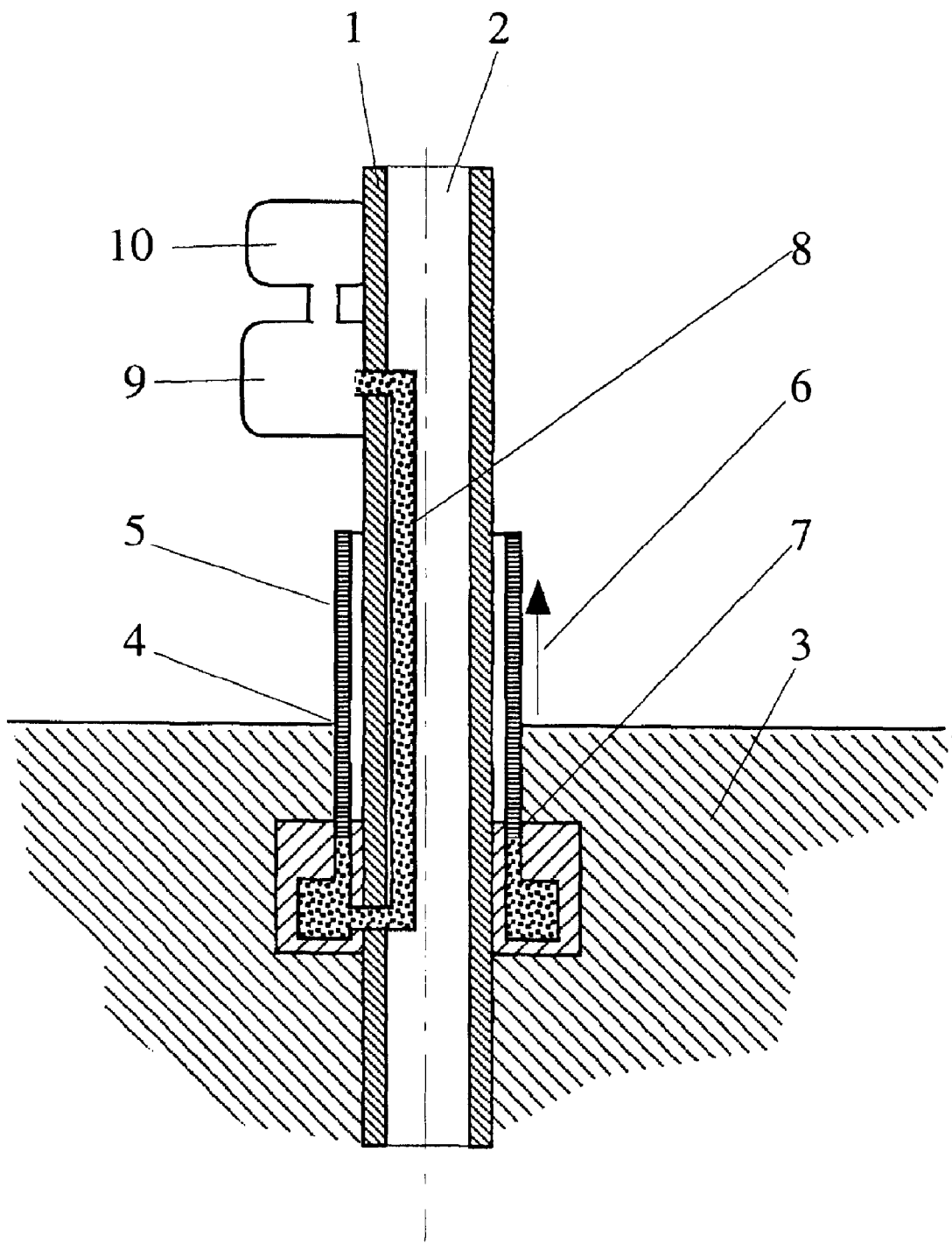
FIG. 1 is a schematic cross sectional view representative of an exemplary embodiment of percutaneous lead of the present invention.

Referring now to the drawings and particularly to FIG. 1, there is shown therein, a schematic cross section of an exemplary embodiment of the present invention. Here a lead 1 enables an exchange of fluids through its lumen 2 from between the outside and the inside of a patient's body 3. At the three-phase line 4, the protective sleeve against infections 5 grows out (in direction of arrow 6) and brings new sterile material to this line 4. A liquid biocompatible polymer material, such as a liquid silicon for example, cures in the extrusion port and grows out continuously or in intervals to form a the protective sleeve against infections 5 around the lead 1.

The liquid polymer material for the sleeve 5 is pumped by a pump 9 from outside of the body of the patient through a tube 8 to an extrusion port 7. The pump 9, is feed with polymer from a reservoir or vessel 10. The vessel 10 can be refilled with a fresh supply of liquid polymer material whenever this is needed. The pump 9 for example can be an electrical micro pump, a battery driven osmotic pump, or a pump which is driven by hand in intervals like days, weeks or months. Another exemplary solution is a mechanical pump with a spring mechanism. In alternative embodiments the pump 9 can be substituted by a pressure reservoir, which pumps the liquid polymer material with gas or vapor pressure.

Inside the body, the cells from surrounding tissue grow at the regenerated protective sleeve against infections. It is known that cells grow well at silicon rubber surfaces. Cells also grow well when supported by a rough surface. Hence it can be suitable to have longitudinal grooves in the extrusion port 7 for generating in the extrusion process a protective sleeve against infections with a larger surface that includes longitudinal ridges and groves. Such a surface further supports the adhesion of cells.

Figure 3:
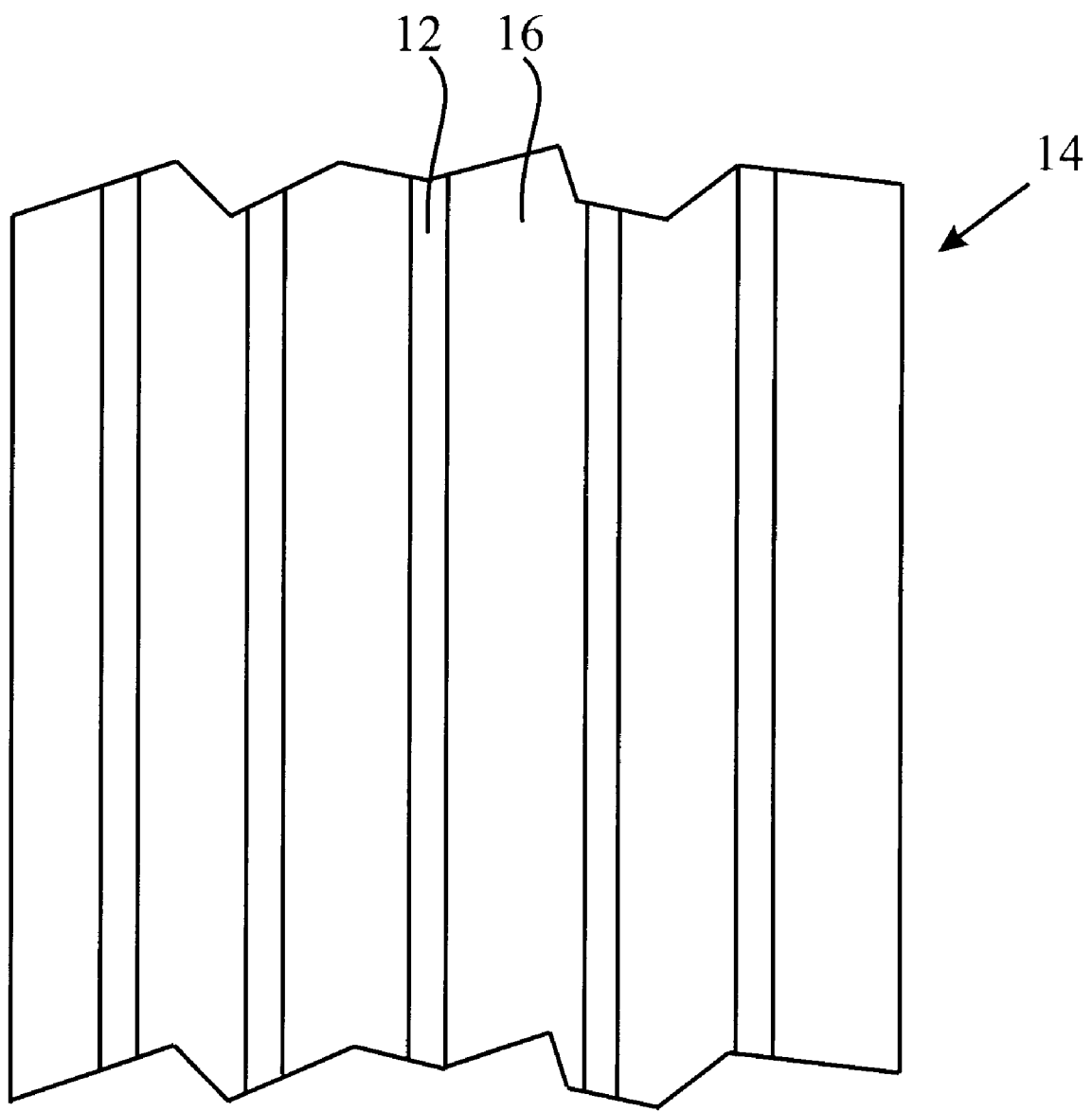
FIG. 3 is a side plan view showing the sterile protective sleeve with a plurality of longitudinal ridges and grooves.

FIG. 3 shows an example of a sterile protective sleeve 14 with a plurality of longitudinal ridges 10 and grooves 12.

Figure 2:
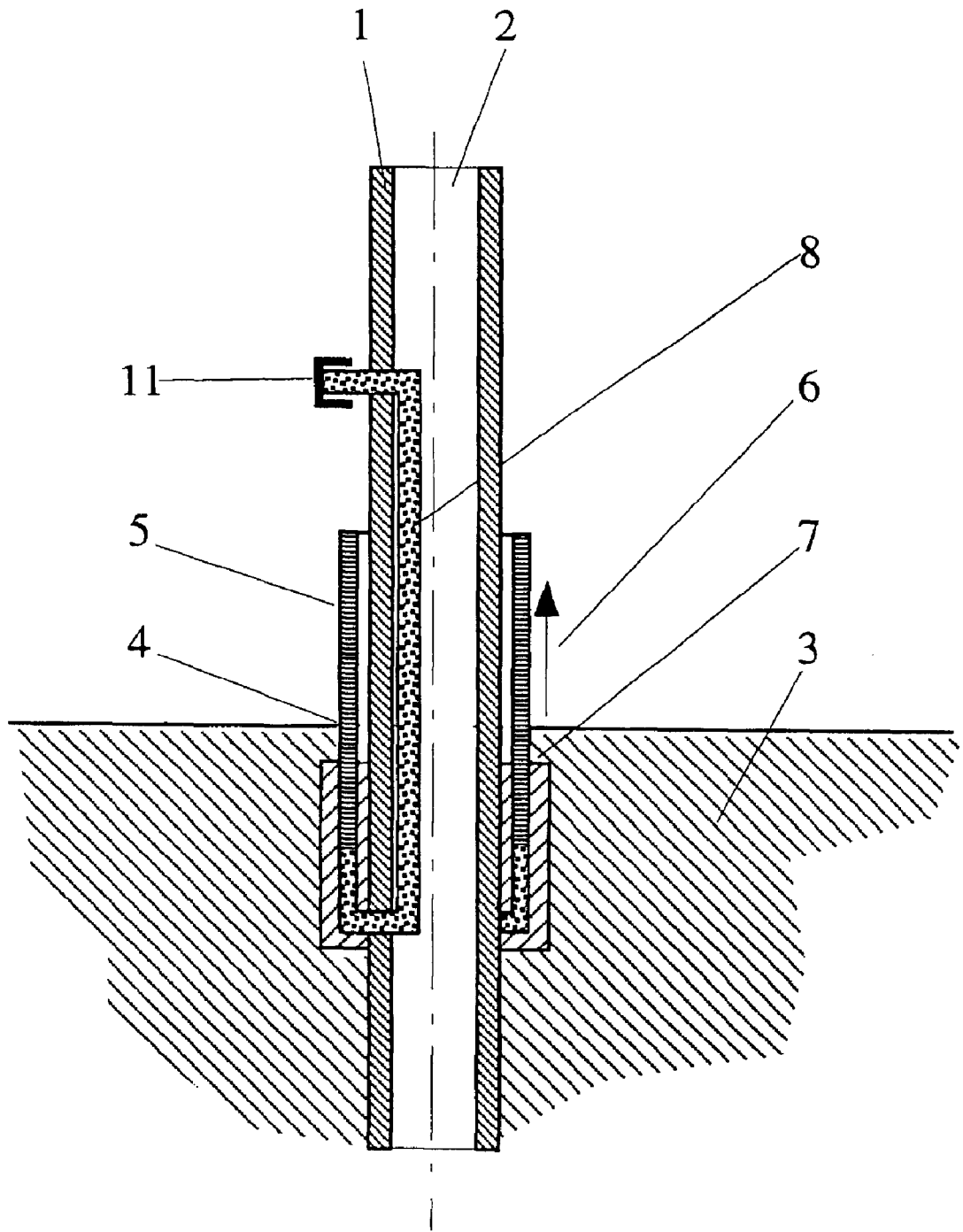
FIG. 2 is a schematic cross sectional view representative of an alternative embodiment of the percutaneous lead of the present invention.

FIG. 2 shows another exemplary embodiment of the present invention. FIG. 2 shows a schematic cross section of the device. In this case, the vessel 10 and the pump 9 are missing. The material for the protective sleeve against infections 5 is pressed in intervals through the tube 8 to the extrusion port 7 by an external pressure. The curing happens from outside to inside.

To prevent a blockage, the extrusion port is tapered. The tube 8 will be closed with the cap 11 between two intervals of filling. This prevents the invading of humidity in the liquid material which may cause premature curing.

In further exemplary embodiments of the present invention, the polymer may be mixed with a catalytic agent prior to the protective sleeve being generated.

Thus the system and method for generation of a protective sleeve against infections for a percutaneous lead through human or animal skin achieves the above stated objectives, eliminates difficulties encountered in the use of prior devices and systems, solves problems and attains the desirable results described herein.

In the foregoing description certain terms have been used for brevity, clarity and understanding, however no unnecessary limitations are to be implied therefrom because such terms are used for descriptive purposes and are intended to be broadly construed. Moreover, the descriptions and illustrations herein are by way of examples and the invention is not limited to the exact details shown and described.

In the following claims any feature described as a means for performing a function shall be construed as encompassing any means known to those skilled in the art to be capable of performing the recited function, and shall not be limited to the structures shown herein or mere equivalents thereof.

Having described the features, discoveries and principles of the invention, the manner in which it is constructed and operated, and the advantages and useful results attained; the new and useful structures, devices, elements, arrangements, parts, combinations, systems, equipment, operations, methods and relationships are set forth in the appended claims.

I claim:

1. A method comprising:
   a) moving into a body of a patient a biocompatible polymer adjacent a portion of an artificial lead, wherein the portion of the artificial lead extends through a tissue of the body of the patient;
   b) generating with the polymer a sterile protective sleeve surrounding the portion of the artificial lead;
   c) directing the sterile protective sleeve to grow in length along the artificial lead in a direction extending out of the body of the patient.

2. The method according to claim 1, wherein the body tissue includes skin.

3. The method according to claim 2, wherein the generating step includes continuously generating the sterile protective sleeve inside the body in the immediate vicinity of the skin.

4. The method according to claim 1, wherein the sterile protective sleeve is operative to permit the attachment and growth of a plurality of cells of the tissue on a surface of the sterile protective sleeve.

5. The method according to claim 1, wherein the sterile protective sleeve includes a biologically active substance that is operative to inhibit infection.

6. The method according to claim 5, wherein the biologically active substances include an antibiotic.

7. A method comprising:
   a) moving into a body of a patient a biocompatible polymer adjacent a portion of an artificial lead, wherein the portion of the artificial lead extends through a tissue of the body of the patient, wherein the polymer is comprised of a fluid material which solidifies to an elastomeric material under the influence of water vapor from the surrounding body tissue; and b) generating with the polymer a sterile protective sleeve adjacent the portion of the artificial lead, wherein the sterile protective sleeve is operative to prevent infections from separating the tissue of the body from the artificial lead.

8. A method comprising:

a) moving into a body of a patient a biocompatible polymer adjacent a portion of an artificial lead, wherein the portion of the artificial lead extends through a tissue of the body of the patient, wherein the body tissue includes skin; and b) intermittently generating with the polymer a sterile protective sleeve adjacent the portion of the artificial lead located, including intermittently generating the sterile protective sleeve inside the body of the patient in the immediate vicinity of the skin, wherein the sterile protective sleeve is operative to prevent infections from separating tissue of the body from the artificial lead.

9. A method comprising:

a) moving into a body of a patient a biocompatible polymer adjacent a portion of an artificial lead, wherein the portion of the artificial lead extends through a tissue of the body of the patient; and b) generating with the polymer a sterile protective sleeve adjacent the portion of the artificial lead, wherein the sterile protective sleeve is operative to permit the attachment and growth of a plurality of cells of the tissue on a surface of the sterile protective sleeve, wherein the surface of the sterile protective sleeve includes a plurality of longitudinal ridges and grooves, wherein the sterile protective sleeve is operative to prevent infections from separating tissue of the body from the artificial lead.

10. A method comprising:

a) moving into a body of a patient a biocompatible polymer adjacent a portion of an artificial lead, wherein the portion of the artificial lead extends through a tissue of the body of the patient;

b) generating with the polymer a sterile protective sleeve adjacent the portion of the artificial lead, wherein the sterile protective sleeve is operative to prevent infections from separating tissue of the body from the artificial lead; and c) periodically replenishing the polymer from a delivering device that is not permanently carried by the patient.

11. A method comprising:

a) moving into a body of a patient a biocompatible polymer adjacent a portion of an artificial lead, wherein the portion of the artificial lead extends through a tissue of the body of the patient;

b) mixing the polymer with a catalytic agent; and c) generating with the polymer a sterile protective sleeve adjacent the portion of the artificial lead, wherein the sterile protective sleeve is operative to prevent infections from separating tissue of the body from the artificial lead.

12. A method comprising:

a) moving into a body of a patient a biocompatible polymer adjacent a portion of an artificial lead, wherein the portion of the artificial lead extends through a tissue of the body of the patient; and b) generating with the polymer a sterile protective sleeve adjacent the portion of the artificial lead, c) growing the sterile protective sleeve in length in a direction that extends outside of the body, wherein the sterile protective sleeve is operative to prevent infections from separating tissue of the body from the artificial lead.

13. The method according to claim 12, further comprising:

c) removing a portion of the sterile protective sleeve that extends outside the body of the patient.

* * * * *